(12) United States Patent
McMahon et al.

(10) Patent No.: US 6,180,631 B1
(45) Date of Patent: Jan. 30, 2001

(54) METHODS OF MODULATING SERINE/THREONINE PROTEIN KINASE FUNCTION WITH 5-AZAQUINOXALINE-BASED COMPOUNDS

(75) Inventors: Gerald McMahon, San Francisco, CA (US); Heinz Weinberger, Sulzbach/Ts; Bernhard Kutscher, Maintal, both of (DE); Harald App, San Francisco, CA (US)

(73) Assignee: Asta Medica Aktiengesellschaft, Dresden (DE)

( * ) Notice: Under 35 U.S.C. 154(b), the term of this patent shall be extended for 0 days.

(21) Appl. No.: 09/166,723

(22) Filed: Oct. 5, 1998

Related U.S. Application Data

(60) Provisional application No. 60/061,123, filed on Oct. 6, 1997.

(51) Int. Cl.[7] .......................... A01N 43/58; A61K 31/50; C07D 471/00; C07D 487/00
(52) U.S. Cl. .................... 514/249; 544/350; 514/253
(58) Field of Search .................... 544/350; 514/253, 514/249

(56) References Cited

U.S. PATENT DOCUMENTS

| | | | |
|---|---|---|---|
| 4,001,017 | * 1/1977 | Baumann et al. | 430/288.1 |
| 4,043,819 | * 8/1977 | Baumann | 430/283.1 |
| 4,999,045 | * 3/1991 | Saupe et al. | 504/215 |
| 5,217,999 | 6/1993 | Levitzki et al. | 514/613 |
| 5,302,606 | 4/1994 | Spada et al. | 514/357 |
| 5,330,992 | 7/1994 | Eissenstat et al. | 514/312 |
| 5,723,462 | * 3/1998 | Albaugh et al. | 514/249 |

FOREIGN PATENT DOCUMENTS

| | | |
|---|---|---|
| 0 566 226 A1 | 10/1993 | (EP) . |
| 91/15495 | 10/1991 | (WO) . |
| 92/20642 | 11/1992 | (WO) . |
| 92/21660 | 12/1992 | (WO) . |
| 94/03427 | 2/1994 | (WO) . |
| 94/14808 | 7/1994 | (WO) . |
| 96/22976 | 8/1996 | (WO) . |
| 96/40116 | 12/1996 | (WO) . |

OTHER PUBLICATIONS

Temple Jr. et al., "Potential Antimitotic Agents . . . ", J. Med. Chem., vol. 33, No. 10, 1990, pp. 3044–3050.*
Elliott et al., "The Isomeric Pyridopyrazines . . . ", Org. Chem., vol. 33, No. 6, 1968, pp. 2393–2397.*
Williams et al., "The Inhibition of Dihydrofolate . . . ", Biochem. Pharm., vol. 29, 1980, pp. 589–595.*
Bonner et al., "Structure and Biological Activity of Human Homologs of the raf/mil Oncogene," *Molecular and Cellular Biology* 5:1400–1407 (1985).
Fodor et al., "A synthesis of adrenaline–like compounds," *J. Amer. Chem. Soc.* 71:1045–1048 (1949).
Folkman, "What is the Evidence that Tumors are Angiogenesis Dependent?" *Journal of the National Cancer Institute* 82:4–6 (1990).
Monia et al., "Antitumor activity of a phosphorothioate antisense oligodeoxynucleotide targeted against C–raf kinase," *Nature Medicine* 2:668–675 (1996).
Morrison et al., "Signal Transduction From Membrane to Cytoplasm: Growth Factors and Membrane–Bound Oncogene Products Increase Raf–1 Phosphorylation and Associated Protein Kinase Activity," *Proc. Natl. Acad. Sci. USA* 85:8855–8859 (1988).
Robbins et al, "Regulation and properties of extracellular signal–regulated protein kinases 1 and 2 in vitro," *J. Biol. Chem.* 268:5097–5106 (1993).

* cited by examiner

*Primary Examiner*—Richard L. Raymond
*Assistant Examiner*—Tamthom N. Truong
(74) *Attorney, Agent, or Firm*—Pillsbury Madison & Sutro LLP

(57) ABSTRACT

The present invention is directed in part towards methods of modulating the function of serine/threonine protein kinases with 5-azaquinoxaline-based compounds. The methods incorporate cells that express a serine/threonine protein kinase, such as RAF. In addition, the invention describes methods of preventing and treating serine/threonine protein kinase-related abnormal conditions in organisms with a compound identified by the invention. Furthermore, the invention pertains to 5-azaquinoxaline compounds and pharmaceutical compositions comprising these compounds.

5 Claims, No Drawings

METHODS OF MODULATING SERINE/THREONINE PROTEIN KINASE FUNCTION WITH 5-AZAQUINOXALINE-BASED COMPOUNDS

RELATED APPLICATIONS

This application claims priority to the U.S. Provisional Application No. 60/061,123, filed Oct. 6, 1997, by McMahon et al., and entitled "METHODS OF MODULATING SERINE/THREONINE PROTEIN KINASE FUNCTION WITH 5-AZAQUINOXALINE-BASED COMPOUNDS" (Lyon & Lyon Docket No. 225/262), which is hereby incorporated by reference in its entirety herein, including any drawings.

BACKGROUND OF THE INVENTION

The following description of the background of the invention is provided to aid in understanding the invention but is not admitted to be prior art to the invention.

Cellular signal transduction is a fundamental mechanism whereby external stimuli regulating diverse cellular processes are relayed to the interior of cells. One of the key biochemical mechanisms of signal transduction involves the reversible phosphorylation of proteins, which enables regulation of the activity of mature proteins by altering their structure and function.

The best characterized protein kinases in eukaryotes phosphorylate proteins on the alcohol moiety of serine, threonine, and tyrosine residues. These kinases largely fall into two groups, those specific for phosphorylating serine and threonine, and those specific for phosphorylating tyrosine. Some kinases, referred to as "dual specificity" kinases, are able to phosphorylate on tyrosine as well as serine/threonine residues.

Protein kinases can also be characterized by their location within the cell. Some kinases are transmembrane receptor proteins capable of binding ligands external to the cell membrane. Binding the ligands alters the receptor protein kinase's catalytic activity. Others are non-receptor proteins lacking a transmembrane domain. Non-receptor protein kinases can be found in a variety of cellular compartments from the inner-surface of the cell membrane to the nucleus.

Many kinases are involved in regulatory cascades where their substrates may include other kinases whose activities are regulated by their phosphorylation state. Ultimately the activity of a downstream effector is modulated by phosphorylation resulting from activation of such a pathway.

The serine/threonine kinase family includes members that regulate many steps of signaling cascades, including cascades controlling cell growth, migration, differentiation, gene expression, muscle contraction, glucose metabolism, cellular protein synthesis, and regulation of the cell cycle.

An example of a non-receptor protein kinase that phosphorylates protein targets on serine and threonine residues is RAF. RAF modulates the catalytic activity of other protein kinases, such as the protein kinase that phosphorylates and thereby activates mitogen activated protein kinase (MAPK). RAF itself is activated by the membrane anchored protein RAS, which in turn is activated in response to ligand activated tyrosine receptor protein kinases such as epidermal growth factor receptor (EGFR) and platelet-derived growth factor receptor (PDGFR). The biological importance of RAF in controlling cellular events is underscored by the finding that altered forms of RAF can cause cancer in organisms. Evidence for importance of RAF in malignancies is provided in Monia et al., 1996, *Nature Medicine* 2: 668, incorporated herein by reference in its entirety including all figures and tables.

In an effort to discover novel treatments for cancer and other diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases are bis monocyclic, bicyclic or heterocyclic aryl compounds (PCT WO 92/20642), vinylene-azaindole derivatives (PCT WO 94/14808), 1-cyclopropyl-4-pyridyl-quinolones (U.S. Pat. No. 5,330,992), styryl compounds (by Levitzki, et al., U.S. Pat. No. 5,217,999, and entitled "Styryl Compounds which Inhibit EGF Receptor Protein Tyrosine Kinase, Lyon & Lyon Docket No. 208/050), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660), and benzylphosphonic acid compounds (PCT WO 91/15495).

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Despite the significant progress that has been made in developing compounds for the treatment of cancer, there remains a need in the art to identify the particular structures and substitution patterns that form the compounds capable of modulating the function of particular protein kinases.

SUMMARY OF THE INVENTION

The present invention is directed in part towards methods of modulating the function of serine/threonine protein kinases with 5-azaquinoxaline-based compounds. The methods incorporate cells that express a serine/threonine protein kinase, such as RAF. In addition, the invention describes methods of preventing and treating serine/threonine protein kinase-related abnormal conditions in organisms with a compound identified by the methods described herein. Furthermore, the invention pertains to pharmaceutical compositions comprising compounds identified by methods of the invention.

I. Methods for Screening Compounds that Modulate Serine/Threonine Protein Kinase Function The methods of the present invention provide means for modulating the function of both receptor and cytosolic serine/threonine protein kinases. These methods provide means of modulating the enzymes both in vitro and in vivo. For in vitro applications, the methods of the invention relate in part to method of identifying compounds that modulate the function of serine/threonine protein kinases.

Thus, in a first aspect, the invention features a method of modulating the function of a serine/threonine protein kinase with an azabenzimidazole-based compound. The azabenzimidazole compound is optionally substituted with organic groups. The method comprises contacting cells expressing the serine/threonine protein kinase with the compound.

The term "function" refers to the cellular role of a serine/threonine protein kinase. The serine/threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "catalytic activity", in the context of the invention, defines the rate at which a protein kinase phosphorylates a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

The term "substrate" as used herein refers to a molecule phosphorylated by a serine/threonine protein kinase. The substrate is preferably a peptide and more preferably a protein. In relation to the protein kinase RAF, preferred substrates are MEK and the MEK substrate MAPK.

The term "activates" refers to increasing the cellular function of a protein kinase. The protein kinase function is preferably the interaction with a natural binding partner and most preferably catalytic activity.

The term "inhibit" refers to decreasing the cellular function of a protein kinase. The protein kinase function is preferably the interaction with a natural binding partner and most preferably catalytic activity.

The term "modulates" refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "complex" refers to an assembly of at least two molecules bound to one another. Signal transduction complexes often contain at least two protein molecules bound to one another. For instance, a protein tyrosine receptor protein kinase, GRB2, SOS, RAF, and RAS assemble to form a signal transduction complex in response to a mitogenic ligand.

The term "natural binding partner" refers to polypeptides that bind to a protein kinase in cells. Natural binding partners can play a role in propagating a signal in a protein kinase signal transduction process. A change in the interaction between a protein kinase and a natural binding partner can manifest itself as an increased or decreased probability that the interaction forms, or an increased or decreased concentration of the protein kinase/natural binding partner complex.

A protein kinase natural binding partner can bind to a protein kinase's intracellular region with high affinity. High affinity represents an equilibrium binding constant on the order of $10^{-6}$ M or less. In addition, a natural binding partner can also transiently interact with a protein kinase intracellular region and chemically modify it. Protein kinase natural binding partners are chosen from a group that includes, but is not limited to, SRC homology 2 (SH2) or 3 (SH3) domains, other phosphoryl tyrosine binding (PTB) domains, guanine nucleotide exchange factors, protein phosphatases, and other protein kinases. Methods of determining changes in interactions between protein kinases and their natural binding partners are readily available in the art.

The term "serine/threonine protein kinase" refers to an enzyme with an amino acid sequence with at least 10% amino acid identity to other enzymes that phosphorylate proteins on serine and threonine residues. A serine/threonine protein kinase catalyzes the addition of phosphate onto proteins on serine and threonine residues. Serine/threonine protein kinases can exist as membrane bound proteins or cytosolic protins.

The term "contacting" as used herein refers to mixing a solution comprising a 5-azaquinoxaline compound of the invention with a liquid medium bathing the cells of the methods. The solution comprising the compound may also comprise another component, such as dimethylsulfoxide (DMSO), which facilitates the uptake of the 5-azaquinoxaline compound or compounds into the cells of the methods. The solution comprising the 5-azaquinoxaline compound may be added to the medium bathing the cells by utilizing a delivery apparatus, such as a pipet-based device or syringe-based device.

The term "5-azaquinoxaline-based compound" refers to a 5-azaquinoxaline organic compound substituted with chemical substituents. 5-azaquinoxaline compounds are of the general structure:

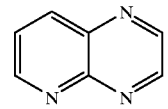

The term "substituted", in reference to the invention, refers to a 5-azaquinoxaline compound that is derivatized with any number of chemical substituents.

In a preferred embodiment, the invention relates to the method of modulating the function of a serine/threonine protein kinase, where the protein kinase is RAF.

The RAF protein kinase phosphorylates protein targets on serine or threonine residues. One such protein target is the protein kinase (MEK) that phosphorylates and consequently activates mitogen activated protein kinase (MAPK). RAF itself is activated by the membrane-bound guanine triphosphate hydrolyzing enzyme RAS in response to mitogen-stimulated receptor protein tyrosine kinases, such as epidermal growth factor receptor (EGFR) and platelet-derived growth factor receptor (PDGFR).

The methods of the present invention can detect compounds that modulate the function of the RAF protein kinase in cells. RAF phosphorylates a protein kinase (MEK) which in turn phosphorylates mitogen-activated protein kinase (MAPK). Assays that monitor only the phosphorylation of MEK by RAF are not sensitive because the phosphorylation levels of MEK are not significant. To overcome this sensitivity dilemma, the phosphorylation of both MEK and MAPK are followed in the assays of the present invention. The MAPK phosphorylation signal amplifies the MEK phosphorylation signal and allows RAF-dependent phosphorylation to be followed in assays, such as enzyme-linked immunosorbant assays. In addition, the assay of the invention is performed in a high throughput format such that many compounds can be rapidly monitored in a short period of time.

In another aspect, the invention describes a method of identifying compounds that modulate the function of serine/threonine protein kinase, comprising the steps of contacting cells expressing the serine/threonine protein kinase with the compound, and monitoring an effect upon the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "effect" describes a change or an absence of a change in cell phenotype or cell proliferation. "Effect" can also describe a change or an absence of a change in the catalytic activity of the protein kinase. "Effect" can also describe a change or an absence of a change in an interaction between the protein kinase and a natural binding partner.

A preferred embodiment of the invention relates to the method of identifying compounds that modulate the function of serine/threonine protein kinase, where the effect is a change or an absence of a change in cell phenotype.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

In another preferred embodiment, the invention relates to the method of identifying compounds that modulate the function of serine/threonine protein kinase, where the effect is a change or an absence of a change in cell proliferation.

The term "cell proliferation" refers to the rate at which a group of cells divides. The number of cells growing in a vessel can be quantified by a person skilled in the art when that person visually counts the number of cells in a defined volume using a common light microscope. Alternatively, cell proliferation rates can be quantified by laboratory apparatae that optically or conductively measure the density of cells in an appropriate medium.

In another preferred embodiment, the invention relates to the method of identifying compounds that modulate the function of serine/threonine protein kinase, where the effect is a change or an absence of a change in the interaction between the serine/threonine protein kinase with a natural binding partner.

The term "interaction", in the context of the invention, describes a complex formed between a protein kinase's intracellular region and a natural binding partner or compound. The term "interaction" can also extend to a complex formed between a compound of the invention with intracellular regions and extracellular regions of the protein kinase under study. Although a cytosolic protein kinase will have no extracellular region, a receptor protein kinase will harbor both an extracellular and an intracellular region.

The term "intracellular region" as used herein refers to the portion of a protein kinase which exists inside a cell. The term "extracellular region" as used herein refers to a portion of a protein kinase which exists outside of the cell.

In a preferred embodiment, the invention relates to the method of identifying compounds that modulate the function of serine/threonine protein kinase that further comprises the following steps:(a) lysing the cells to render a lysate comprising serine/threonine protein kinase; (b) adsorbing the serine/threonine protein kinase to an antibody; (c) incubating the adsorbed serine/threonine protein kinase with a substrate or substrates; and (d) adsorbing the substrate or substrates to a solid support or antibody. The step of monitoring the effect on the cells comprises measuring the phosphate concentration of the substrate or substrates.

The term "lysing" as used herein refers to a method of disrupting the integrity of a cell such that its interior contents are liberated. Cell lysis is accomplished by many techniques known to persons skilled in the art. The method is accomplished preferably by sonication or cell sheering techniques and more preferably by detergent techniques.

The term "antibody" as used herein refers to a protein molecule that specifically binds a protein kinase. An antibody preferably binds to one class of protein kinase and more preferably specifically binds to the RAF protein kinase.

The term "specifically binds" as used herein refers to an antibody that binds a protein kinase with higher affinity than another protein kinase or cellular protein. An antibody that specifically binds to a protein kinase will bind a higher concentration of the specific protein kinase than any other protein kinase or cellular protein.

The term "adsorbing" as used herein refers to the binding of a molecule to the surface of an antibody or solid support. Examples of solid supports are chemically modified cellulose, such as phosphocellulose, and nylon. Antibodies can be linked to solid supports using techniques well known to individuals of ordinary skill in the art. See, e.g., Harlo & Lane, *Antibodies, A Laboratory Manual*, 1989, Cold Spring Harbor Laboratories.

The term "measuring the phosphate concentration" as used herein refers to techniques commonly known to persons of ordinary skill in the art. These techniques can involve quantifying the concentration of phosphate concentrations within a substrate or determining relative amounts of phosphate within a substrate. These techniques can include adsorbing the substrate to a membrane and detecting the amount of phosphate within the substrate by radioactive measurements.

In another preferred embodiment, the invention relates to the method of identifying compounds that modulate the function of serine/threonine protein kinase that further comprises the following steps: (a) lysing the cells to render a lysate comprising RAF; (b) adsorbing the RAF to an antibody; (c) incubating the adsorbed RAF with MEK and MAPK; and (d) adsorbing the MEK and MAPK to a solid support or antibody or antibodies. The step of measuring the effect on the cells comprises monitoring the phosphate concentration of said MEK and MAPK.

In a preferred embodiment, the invention relates to the method of identifying compounds that modulate the function of serine/threonine protein kinase, where the 5-azaquinoxaline-based compound has a structure set forth in formula I as defined herein or any of the subgroups thereof set forth herein.

The term "compound" refers to the compound or a pharmaceutically acceptable salt, ester, amide, prodrug, isomer, or metabolite, thereof.

The term "pharmaceutically acceptable salt" refers to a formulation of a compound that does not abrogate the biological activity and properties of the compound. Pharmaceutical salts can be obtained by reacting a compound of the invention with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

In another preferred embodiment, the invention relates to the method of identifying compounds that modulate the function of serine/threonine protein kinase, where the 5-azaquinoxaline-based compound has a structure set forth in formula I, where the 5-azaquinoxaline-based compound is selected from the group consisting of SAQAR compounds.

The term "SAQAR compounds" refers to the group of 5-azaquinoxaline-based compounds having a structure set forth in formula I and numbered A-1 through A-90 in the following table:

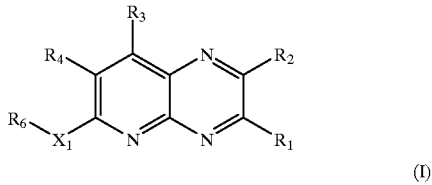

(I)

| Compound No. | $R_2$ | $R_1$ | $R_6X_1$ |
|---|---|---|---|
| A-1. | H | 4-hydroxyphenyl | phenylamino |
| A-2. | H | 4-hydroxyphenyl | benzylamino |
| A-3. | methyl | phenyl | methoxy |
| A-4. | phenyl | phenyl | methoxy |
| A-5. | methyl | phenyl | 4-fluorobenzylamino |
| A-6. | phenyl | phenyl | 4-fluorobenzylamino |
| A-7. | H | phenyl | phenylamino |
| A-8. | H | 4-hydroxyphenyl | 2-carboxybenzylamino |
| A-9. | H | 4-hydroxyphenyl | 3-carboxybenzylamino |
| A-10. | H | 4-hydroxyphenyl | 4-carboxybenzylamino |
| A-11. | H | 4-hydroxyphenyl | 2-nitrobenzylamino |
| A-12. | H | 4-hydroxyphenyl | 3-nitrobenzylamino |
| A-13. | H | 4-hydroxyphenyl | 4-nitrobenzylamino |
| A-14. | H | 4-hydroxyphenyl | 2-methylbenzylamino |
| A-15. | H | 4-hydroxyphenyl | 3-methylbenzylamino |
| A-16. | H | 4-hydroxyphenyl | 4-methylbenzylamino |
| A-17. | H | 4-hydroxyphenyl | 2-chlorobenzylamino |
| A-18. | H | 4-hydroxyphenyl | 3-chlorobenzylamino |
| A-19. | H | 4-hydroxyphenyl | 4-chlorobenzylamino |
| A-20. | H | 4-hydroxyphenyl | 2-fluorobenzylamino |
| A-21. | H | 4-hydroxyphenyl | 3-fluorobenzylamino |
| A-22. | H | 4-hydroxyphenyl | 4-fluorobenzylamino |
| A-23. | H | 4-hydroxyphenyl | 2-(trifluoromethyl)benzylamino |
| A-24. | H | 4-hydroxyphenyl | 3-(trifluoromethyl)benzylamino |
| A-25. | H | 4-hydroxyphenyl | 4-(trifluoromethyl)benzylamino |
| A-26. | H | 4-hydroxyphenyl | phenethyl-1-amino |
| A-27. | H | 4-hydroxyphenyl | 2-carboxyphenylamino |
| A-28. | H | 4-hydroxyphenyl | 3-carboxyphenylamino |
| A-29. | H | 4-hydroxyphenyl | 4-carboxyphenylamino |
| A-30. | H | 4-hydroxyphenyl | 2-nitrophenylamino |
| A-31. | H | 4-hydroxyphenyl | 3-nitrophenylamino |
| A-32. | H | 4-hydroxyphenyl | 4-nitrophenylamino |
| A-33. | H | 4-hydroxyphenyl | 2-methylphenylamino |
| A-34. | H | 4-hydroxyphenyl | 3-methylphenylamino |
| A-35. | H | 4-hydroxyphenyl | 4-methylphenylamino |
| A-36. | H | 4-hydroxyphenyl | 2-chlorophenylamino |
| A-37. | H | 4-hydroxyphenyl | 3-chlorophenylamino |
| A-38. | H | 4-hydroxyphenyl | 4-chlorophenylamino |
| A-39. | H | 4-hydroxyphenyl | 2-fluorophenylamino |
| A-40. | H | 4-hydroxyphenyl | 3-fluorophenylamino |
| A-41. | H | 4-hydroxyphenyl | 4-fluorophenylamino |
| A-42. | H | 4-hydroxyphenyl | 2-(trifluoromethyl)phenylamino |
| A-43. | H | 4-hydroxyphenyl | 3-(trifluoromethyl)phenylamino |
| A-44. | H | 4-hydroxyphenyl | 4-(trifluoromethyl)phenylamino |
| A-45. | H | 4-hydroxyphenyl | pyrid-2-amino |
| A-46. | H | 4-hydroxyphenyl | pyrid-3-amino |
| A-47. | H | 4-hydroxyphenyl | pyrid-4-amino |
| A-48. | H | 4-hydroxyphenyl | pyrid-2-methylamino |
| A-49. | H | phenyl | 2-carboxybenzylamino |
| A-50. | H | phenyl | 3-carboxybenzylamino |
| A-51. | H | phenyl | 4-carboxybenzylamino |
| A-52. | H | phenyl | 2-nitrobenzylamino |
| A-53. | H | phenyl | 3-nitrobenzylamino |
| A-54. | H | phenyl | 4-nitrobenzylamino |
| A-55. | H | phenyl | 2-methylbenzylamino |
| A-56. | H | phenyl | 3-methylbenzylamino |
| A-57. | H | phenyl | 4-methylbenzylamino |
| A-58. | H | phenyl | 2-chlorobenzylamino |
| A-59. | H | phenyl | 3-chlorobenzylamino |
| A-60. | H | phenyl | 4-chlorobenzylamino |
| A-61. | H | phenyl | 2-fluorobenzylamino |
| A-62. | H | phenyl | 3-fluorobenzylamino |
| A-63. | H | phenyl | 4-fluorobenzylamino |
| A-64. | H | phenyl | 2-(trifluoromethyl)benzylamino |
| A-65. | H | phenyl | 3-(trifluoromethyl)benzylamino |
| A-66. | H | phenyl | 4-(trifluoromethyl)benzylamino |
| A-67. | H | phenyl | phenethyl-1-amino |
| A-68. | H | phenyl | 2-carboxyphenylamino |
| A-69. | H | phenyl | 3-carboxyphenylamino |
| A-70. | H | phenyl | 4-carboxyphenylamino |
| A-71. | H | phenyl | 2-nitrophenylamino |
| A-72. | H | phenyl | 3-nitrophenylamino |
| A-73. | H | phenyl | 4-nitrophenylamino |
| A-74. | H | phenyl | 2-methylphenylamino |
| A-75. | H | phenyl | 3-methylphenylamino |
| A-76. | H | phenyl | 4-methylphenylamino |
| A-77. | H | phenyl | 2-chlorophenylamino |
| A-78. | H | phenyl | 3-chlorophenylamino |
| A-79. | H | phenyl | 4-chlorophenylamino |
| A-80. | H | phenyl | 2-fluorophenylamino |
| A-81. | H | phenyl | 3-fluorophenylamino |
| A-82. | H | phenyl | 4-fluorophenylamino |
| A-83. | H | phenyl | 2-(trifluoromethyl)phenylamino |
| A-84. | H | phenyl | 3-(trifluoromethyl)phenylamino |
| A-85. | H | phenyl | 4-(trifluoromethyl)phenylamino |
| A-86. | H | phenyl | pyrid-2-amino |
| A-87. | H | phenyl | pyrid-3-amino |
| A-88. | H | phenyl | pyrid-4-amino |
| A-89. | H | phenyl | pyrid-2-methylamino |
| A-90. | H | 4-methoxyphenyl | phenylamino |

II. Methods of Preventing or Treating Abnormal Conditions

In another aspect, the invention features a method of preventing or treating an abnormal condition in an organism. The method comprises the following steps: (a) administering a compound of the invention, as specified herein by formula I with any of the constraints provided herein, to an organism; and (b) promoting or disrupting the abnormal interaction.

The term "organism" relates to any living entity comprising at least one cell. An organism can be as simple as one eukaryotic cell or as complex as a mammal. In preferred embodiments, an organism refers to humans or mamals.

The term "preventing" refers to the method of the invention decreasing the probability, or eliminating the possibility, that an organism contracts or develops the abnormal condition.

The term "treating" refers to the method of the invention having a therapeutic effect and at least partially alleviating or abrogating the abnormal condition in the organism.

The term "therapeutic effect" refers to the inhibition of cell growth causing or contributing to an abnormal condition (e.g. cancer). The term "therapeutic effect" also refers to the inhibition of growth factors causing or contributing to the abnormal condition. A therapeutic effect relieves to some extent one or more of the symptoms of the abnormal condition. In reference to the treatment of a cancer, a therapeutic effect refers to one or more of the following: (a) a reduction in tumor size; (b) inhibition (i.e., slowing or stopping) tumor metastasis; (c) inhibition of tumor growth; and (d) relieving to some extent one or more of the symptoms associated with the abnormal condition. Compounds demonstrating efficacy against leukemias can be identified as described herein, except that rather than inhibiting metastasis, the compounds may instead slow or decrease cell proliferation or cell growth.

The term "abnormal condition" refers to a function in the cells or tissues of an organism that deviates from their normal functions in that organism. An abnormal condition can relate to cell proliferation, cell differentiation, or cell survival.

Aberrant cell proliferative conditions include cancers such as fibrotic and mesangial disorders, abnormal angiogenesis and vasculogenesis, wound healing, psoriasis, diabetes mellitus, and inflammation.

Aberrant differentiation conditions include, but are not limited to neurodegenerative disorders, slow wound healing rates, and tissue grafting techniques.

Aberrant cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

Cell proliferation, differentiation, and survival are phenomena simply measured by methods in the art. These methods can involve observing the number of cells or the appearance of cells under a microscope with respect to time (for example, days).

The term "administering" relates broadly to the provision to an organism and more specifically to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

In a preferred embodiment, the invention relates to a method of preventing or treating an abnormal condition in an organism, where the 5-azaquinoxaline-based compound has a structure set forth in formula I as defined herein or any of the subgroups thereof set forth herein.

In other preferred embodiments, the invention relates to a method of preventing or treating an abnormal condition in an organism, where the 5-azaquinoxaline-based compound, having a structure set forth in formula I, is selected from the group consisting of SAQAR compounds.

In another preferred embodiment, the invention relates to a method of preventing or treating an abnormal condition in an organism, where the organism is a mammal.

The term "mammal" refers preferably to such organisms as mice, rats, rabbits, guinea pigs, and goats, more preferably to monkeys and apes, and most preferably to humans.

In yet another preferred embodiment, the invention relates to a method of preventing or treating an abnormal condition in an organism, where the abnormal condition is cancer or a fibrotic disorder.

In another preferred embodiment, the invention relates to a method of preventing or treating an abnormal condition in an organism, where the cancer is selected from the group consisting of lung cancer, ovarian cancer, breast cancer, brain cancer, intra-axial brain cancer, colon cancer, prostate cancer, sarcoma, Kaposi's sarcoma, melanoma, and glioma.

In still another preferred embodiment, the invention relates to a method of preventing or treating an abnormal condition in an organism, where the method applies to an abnormal condition associated with an aberration in a signal transduction pathway characterized by an interaction between a serine/threonine protein kinase and a natural binding partner.

The term "signal transduction pathway" refers to the propagation of a signal. In general, an extracellular signal is transmitted through the cell membrane to become an intracellular signal. This signal can then stimulate a cellular response. The term also encompases signals that are propagated entirely within a cell. The polypeptide molecules involved in signal transduction processes are typically receptor and non-receptor protein kinases, receptor and non-receptor protein phosphatases, nucleotide exchange factors, and transcription factors.

The term "aberration", in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "promoting or disrupting the abnormal interaction" refers to a method that can be accomplished by administering a compound of the invention to cells or tissues in an organism. A compound can promote an interaction between a protein kinase and natural binding partners by forming favorable interactions with multiple atoms at the complex interface. Alternatively, a compound can inhibit an interaction between a protein kinase and natural binding partners by compromising favorable interactions formed between atoms at the complex interface.

In another preferred embodiment, the invention relates to a method of preventing or treating an abnormal condition in an organism, where the serine/threonine protein kinase is RAF.

III. Compounds and Pharmaceutical Compositions of the Invention

In another aspect, the invention features 5-azaquinoxaline compounds having structures set forth in formula I:

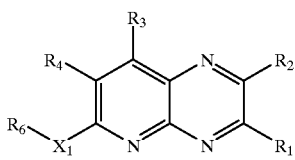

(I)

where
(a) $R_1$, $R_2$, and $R_6$ are independently selected from the group consisting of
  (i) hydrogen;
  (ii) saturated or unsaturated alkyl;
  (iii) an amine of formula $NX_2X_3$, where $X_2$ and $X_3$ are independently selected from the group consisting of hydrogen, saturated or unsaturated alkyl, and five-membered or six-membered aryl or heteroaryl ring moieties;
  (iv) halogen or trihalomethyl;
  (v) a ketone of formula —CO—$X_4$, where $X_4$ is selected from the group consisting of hydrogen, alkyl, and five-membered or six-membered aryl or heteroaryl moieties;
  (vi) a carboxylic acid of formula —$(X_5)_n$—COOH or ester of formula —$(X_6)_n$—COO—$X_7$, where $X_5$, $X_6$, and $X_7$ are independently selected from the group consisting of alkyl and five-membered or six-membered aryl or heteroaryl moieties and where n is 0 or 1;
  (vii) an alcohol of formula $(X_8)_n$—OH or an alkoxy moiety of formula —$(X_8)_n$—O—$X_9$, where $X_8$ and $X_9$ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester and where n is 0 or 1;
  (viii) an amide of formula —NHCO$X_{10}$, where $X_{10}$ is selected from the group consisting of alkyl, hydroxyl, and five-membered or six-membered aryl or heteroaryl ring moieties, where the ring is optionally substituted with one or more substituents independently selected from the group consisting of alkyl, halogen, trihalomethyl, carboxylate, nitro, or ester;
  (ix) —SO$_2$N$X_{11}X_{12}$, where $X_{11}$ and $X_{12}$ are selected from the group consisting of hydrogen, alkyl, and five-membered or six-membered aryl or heteroaryl ring moieties;
  (x) a five-membered or six-membered aryl or heteroaryl ring moiety optionally substituted with one, two, or three substituents independently selected from the group consisting of alkyl, halogen, trihalomethyl, carboxylate, nitro, and ester moieties;
  (xi) an aldehyde of formula —CO—H; and
  (xii) a sulfone of formula —SO$_2$—$X_{13}$, where $X_{13}$ is selected from the group consisting of saturated or unsaturated alkyl and five-membered or six-membered aryl or heteroaryl moieties; and
(b) $X_1$ is selected from the group consisting of nitrogen, sulfur, and oxygen.

The term "saturated alkyl" refers to an alkyl moiety that does not contain any alkene or alkyne moieties. The alkyl moiety may be branched or non-branched.

The term "unsaturated alkyl" refers to an alkyl moiety that contains at least one alkene or alkyne moiety. The alkyl moiety may be branched or non-branched.

The term "amine" refers to a chemical moiety of formula $NR_1R_2$ where $R_1$ and $R_2$ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "aryl" refers to an aromatic group which has at least one ring having a conjugated pi electron system and includes both carbocyclic aryl (e.g. phenyl) and heterocyclic aryl groups (e.g. pyridine). The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaryl" refers to an aryl group which contains at least one heterocyclic ring.

The term "halogen" refers to an atom selected from the group consisting of fluorine, chlorine, bromine, and iodine.

The term "ketone" refers to a chemical moiety with formula —(R)n—CO—R', where R and R' are selected from the group consisting of saturated or unsaturated alkyl and five-membered or six-membered aryl or heteroaryl moieties and where n is 0 or 1.

The term "carboxylic acid" refers to a chemical moiety with formula —(R)n—COOH, where R is selected from the group consisting of saturated or unsaturated alkyl and five-membered or six-membered aryl or heteroaryl moieties and where n is 0 or 1.

The term "ester" refers to a chemical moiety with formula —(R)n—COOR', where R and R' are independently selected from the group consisting of saturated or unsaturated alkyl and five-membered or six-membered aryl or heteroaryl moieties and where n is 0 or 1.

The term "alcohol" refers to a chemical substituent of formula —ROH, where R is selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "amide" refers to a chemical substituent of formula —NHCOR, where R is selected from the group consisting of hydrogen, alkyl, hydroxyl, and five-membered or six-membered aryl or heteroaryl ring moieties, where the ring is optionally substituted with one or more substituents independently selected from the group consisting of alkyl, halogen, trihalomethyl, carboxylate, nitro, or ester.

The term "alkoxy moiety" refers to a chemical substituent of formula —OR, where R is hydrogen or a saturated or unsaturated alkyl moiety.

The term "aldehyde" refers to a chemical moiety with formula —(R)n—CHO, where R is selected from the group consisting of saturated or unsaturated alkyl and five-membered or six-membered aryl or heteroaryl moieties and where n is 0 or 1.

The term "sulfone" refers to a chemical moiety with formula —SO$_2$—R, where R is selected from the group consisting of saturated or unsaturated alkyl and five-membered or six-membered aryl or heteroaryl moieties.

In another preferred embodiment, the invention relates to a 5-azaquinoxaline-based compound having a structure set forth in formula I, where $R_3$ and $R_4$ are independently selected from the group consisting of hydrogen and saturated or unsaturated alkyl.

In yet another preferred embodiment, the invention relates to a 5-azaquinoxaline-based compound having a structure set forth in formula I, where $R_3$ and $R_4$ are hydrogen.

In other preferred embodiments, the invention relates to a 5-azaquinoxaline-based compound having a structure set forth in formula I, where $R_1$ and $R_2$ are selected from the group consisting of hydrogen, saturated or unsaturated alkyl, a five-membered or six-membered aryl or heteroaryl ring moiety optionally substituted with one, two, or three substituents independently selected from the group consisting of alkyl, halogen, trihalomethyl, hydroxy, alkoxy, carboxylate, nitro, and ester moieties.

In still other preferred embodiments, the invention relates to a 5-azaquinoxaline-based compound having a structure set forth in formula I, where $R_1$ is phenyl optionally substituted with one, two, or three substituents independently selected from the group consisting of alkyl, halogen, hydroxy, and alkoxy moieties.

In another preferred embodiment, the invention relates to a 5-azaquinoxaline-based compound having a structure set forth in formula I, where $R_1$ is phenyl.

In yet another preferred embodiment, the invention relates to a 5-azaquinoxaline-based compound having a structure set forth in formula I, where $R_1$ is 4-hydroxyphenyl.

In other preferred embodiments, the invention relates to a 5-azaquinoxaline-based compound having a structure set forth in formula I, where $R_2$ is selected from the group consisting of hydrogen, saturated or unsaturated alkyl, and phenyl optionally substituted with one, two, or three substituents independently selected from the group consisting of alkyl, halogen, hydroxy, and alkoxy moieties.

In another preferred embodiment, the invention relates to a 5-azaquinoxaline-based compound having a structure set forth in formula I, where $R_2$ is hydrogen.

In yet another preferred embodiment, the invention relates to a 5-azaquinoxaline-based compound having a structure set forth in formula I, where $R_2$ is methyl.

In still another preferred embodiment, the invention relates to a 5-azaquinoxaline-based compound having a structure set forth in formula I, where $R_2$ is phenyl.

In another preferred embodiment, the invention relates to a 5-azaquinoxaline-based compound having a structure set forth in formula I, where the $X_1$ is nitrogen or oxygen.

In yet another preferred embodiment, the invention relates to a 5-azaquinoxaline-based compound having a structure set forth in formula I, where the $X_1$ is oxygen.

In yet another preferred embodiment, the invention relates to a 5-azaquinoxaline-based compound having a structure set forth in formula I, where the $X_1$ is nitrogen.

In other preferred embodiments, the invention relates to a 5-azaquinoxaline-based compound having a structure set forth in formula I, where $R_6$ is selected from the group consisting of hydrogen; saturated or unsaturated alkyl optionally substituted with a five-membered or six-membered aryl or heteroaryl ring moiety optionally substituted with one, two, or three substituents independently selected from the group consisting of alkyl, halogen, trihalomethyl, hydroxy, alkoxy, carboxylate, nitro, and ester moieties; and a five-membered or six-membered aryl or heteroaryl ring moiety optionally substituted with one, two, or three substituents independently selected from the group consisting of alkyl, halogen, trihalomethyl, hydroxy, alkoxy, carboxylate, nitro, and ester moieties.

In still other preferred embodiments, the invention relates to a 5-azaquinoxaline-based compound having a structure set forth in formula I, where the $R_6$ and $X_1$ moieties taken together form a compound which is selected from the group consisting of SAQAR substituents.

The term "SAQAR substituents" refers to the group of substituents consisting of methoxy, benzylamino, 4-fluorobenzylamino, 2-carboxybenzylamino, 3-carboxybenzylamino, 4-carboxybenzylamino, 2-nitrobenzylamino, 3-nitrobenzylamino, 4-nitrobenzylamino, 2-methylbenzylamino, 3-methylbenzylamino, 4-methylbenzylamino, 2-chlorobenzylamino, 3-chlorobenzylamino, 4-chlorobenzylamino, 2-fluorobenzylamino, 3-fluorobenzylamino, 4-fluorobenzylamino, 2-(trifluoromethyl)benzylamino, 3-(trifluoromethyl)benzylamino, 4-(trifluoromethyl)benzylamino, phenethyl-1-amino, phenylamino, 2-carboxyphenylamino, 3-carboxyphenylamino, 4-carboxyphenylamino, 2-nitrophenylamino, 3-nitrophenylamino, 4-nitrophenylamino, 2-methylphenylamino, 3-methylphenylamino, 4-methylphenylamino, 2-chlorophenylamino, 3-chlorophenylamino, 4-chlorophenylamino, 2-fluorophenylamino, 3-fluorophenylamino, 4-fluorophenylamino, 2-(trifluoromethyl)phenylamino, 3-(trifluoromethyl)phenylamino, 4-(trifluoromethyl)phenylamino, pyrid-2-amino, pyrid-3-amino, pyrid-4-amino, and pyrid-2-methylamino.

The term "benzylamino" refers to a group having a structure set forth in the following formula:

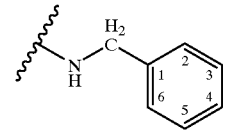

where the aryl ring may be optionally substituted in the 2, 3, or 4 position.

The term "phenylamino" refers to a group having a structure set forth in the following formula:

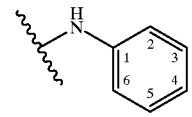

where the aryl ring may be optionally substituted in the 2, 3, or 4 position.

The term "phenethyl-1-amino" refers to a group having a structure set forth in the following formula:

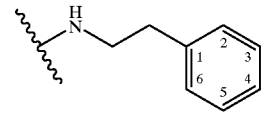

The term "pyrid-2-amino" refers to a pyridine ring which is substituted with an NH group in the 2 position. Similarly, the terms "pyrid-3-amino" and "pyrid-4-amino" refer to a pyridine ring which is substituted with an NH group in the 3 and 4 positions, respectively.

In yet another preferred embodiment, the invention relates to a 5-azaquinoxaline-based compound having a structure set forth in formula I, where the 5-azaquinoxaline-based compound is selected from the group consisting of SAQAR compounds.

IV. Synthetic Methods of the Invention

In another aspect, the invention features a pharmaceutical composition comprising a compound having a structure of formula I as defined herein or any of the subgroups thereof set forth herein, or its salt, and a physiologically acceptable carrier or diluent.

In a preferred embodiment, the invention relates to a pharmaceutical composition, where the 5-azaquinoxaline-based compound is selected from the group consisting of SAQAR compounds.

The term "pharmaceutical composition" refers to a mixture of a 5-azaquinoxaline compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In yet another aspect, the invention features a method for synthesizing a compound of the invention, comprising the steps of: (a) reacting 2-amino-6-chloro-3-nitropyridine with a second reactant in a solvent and in the presence of a base, where the second reactant is selected from the group consisting of an alcohol and an amine to yield the first intermediate; (b) reacting the first intermediate with a 1,2-dione in the presence of a catalyst and a reducing agent; and (d) purifying the final product.

The term "1,2-dione" refers to a chemical moiety of the formula $R_1$—C(O)C(O)—$R_2$, where $R_1$ and $R_2$ are independently selected from the group consisting of hydrogen; saturated or unsaturated alkyl optionally substituted with a five-membered or six-membered aryl or heteroaryl ring moiety optionally substituted with one, two, or three substituents independently selected from the group consisting of alkyl, halogen, trihalomethyl, hydroxy, alkoxy, carboxylate, nitro, and ester moieties; and a five-membered or six-membered aryl or heteroaryl ring moiety optionally substituted with one, two, or three substituents independently selected from the group consisting of alkyl, halogen, trihalomethyl, hydroxy, alkoxy, carboxylate, nitro, and ester moieties.

In a preferred embodiment, the invention relates to the method of synthesizing a compound of the invention where the solvent is n-butanol.

In another preferred embodiment, the invention relates to the method of synthesizing a compound of the invention where the base is powdered potassium carbonate.

In yet another preferred embodiment, the invention relates to the method of synthesizing a compound of the invention where the second reactant is selected from the group consisting of SAQAR reactants.

The term "SAQAR reactants" refers to the group of reactants consisting of methanol, benzylamine, 4-fluorobenzylamine, 2-carboxybenzylamine, 3-carboxybenzylamine, 4-carboxybenzylamine, 2-nitrobenzylamine, 3-nitrobenzylamine, 4-nitrobenzylamine, 2-methylbenzylamine, 3-methylbenzylamine, 4-methylbenzylamine, 2-chlorobenzylamine, 3-chlorobenzylamine, 4-chlorobenzylamine, 2-fluorobenzylamine, 3-fluorobenzylamine, 4-fluorobenzylamine, 2-(trifluoromethyl)benzylamine, 3-(trifluoromethyl)benzylamine, 4-(trifluoromethyl)benzylamine, phenethyl-1-amine, aniline, 2-carboxyaniline, 3-carboxyaniline, 4-carboxyaniline, 2-nitroaniline, 3-nitroaniline, 4-nitroaniline, 2-toluidine, 3-toluidine, 4-toluidine, 2-chloroaniline, 3-chloroaniline, 4-chloroaniline, 2-fluoroaniline, 3-fluoroaniline, 4-fluoroaniline, 2-(trifluoromethyl)aniline, 3-(trifluoromethyl)aniline , 4-(trifluoromethyl)aniline, 2-aminopyridine, 3-aminopyridine, 4-aminopyridine, and 2-methylaminopyridine.

In still another preferred embodiment, the invention relates to the method of synthesizing a compound of the invention where the third reactant is selected from the group consisting of 4-hydroxyphenylglyoxal, 1-phenyl-1,2-propanedione, and benzil.

The term "catalyst" as used herein refers to a chemical molecule, that when added to a group of reactants, can increase the rate at which the reactants react to form products. Many types of catalysts are well known to persons of ordinary skill in the art.

In a preferred embodiment, the invention relates to the methods for synthesizing compounds of the invention, where the reducing agent is hydrogen.

In another preferred embodiment, the invention relates to the methods for synthesizing compounds of the invention, where the catalyst is Raney nickel.

The summary of the invention described above is non-limiting and other features and advantages of the invention will be apparent from the following description of the preferred embodiments, and from the claims.

DESCRIPTION OF THE PREFERRED EMBODIMENTS

The present invention is directed in part towards methods of modulating the function of serine/threonine protein kinases with 5-azaquinoxaline-based compounds. In addition, the invention relates in part to methods for identifying compounds that modulate the function of serine/threonine protein kinases. The methods incorporate cells that express a serine/threonine protein kinase, such as RAF.

RAF is a non-receptor protein kinase that is recruited to the cell membrane when it binds to activated RAS, a guanine triphosphate hydrolyzing enzyme. RAS is activated when an activated receptor protein tyrosine kinase, such as EGFR or PDGFR, bind to an adaptor protein, GRB2, and a guanine nucleotide exchange factor, SOS. SOS removes guanine diphosphate from RAS, replaces it with guanine triphosphate, and thereby activates RAS. RAS then binds RAF and consequently activates RAF. RAF may then phosphorylate other protein targets on serine and threonine residues, such as the kinase (MEK) that phosphorylates and consequently activates mitogen-activated protein kinase (MAPK). Thus, RAF serves as an intermediary controlling factor in mitogen-activated signal transduction.

Due to the important regulatory role of RAF in cells, modifications to the amino acid sequence of RAF can alter its function and consequently modify cellular behavior. RAF's role in cell proliferation is underscored by the observation that mutations to RAF's amino acid sequence have been associated with tumors and cancers. Because the mutations to RAF that give rise to cancer in cells lead to RAF molecules that display unregulated catalytic activity, inhibitors of RAF may alleviate or even abrogate the cell proliferation that leads to cancer in these cells.

Methods of the present invention can detect compounds that modulate the function of the protein kinase RAF in cells. RAF phosphorylates a protein kinase (MEK) which in turn phosphorylates mitogen-activated protein kinase (MAPK). Assays that monitor only the phosphorylation of MEK by RAF are not sensitive because the phosphorylation levels of MEK are not significant. To overcome this sensitivity dilemma, the phosphorylation of both MEK and MAPK are followed in the assays of the present invention. The MAPK phosphorylation signal amplifies the MEK phosphorylation signal and allows RAF-dependent phosphorylation to be followed in enzyme-linked immunosorbant assays. In addition, the assay of the invention is preferably performed in a high throughput format such that many compounds can be rapidly monitored in a short period of time.

The methods of the present invention have identified compounds that inhibit the function of RAF protein kinase. These compounds are 5-azaquinoxaline-based derivatives. Although 5-azaquinoxaline-based derivatives have been tested for their ability to inhibit enzymes involved with nucleotide synthesis in bacteria, many of these compounds have not yet been significantly explored with respect to protein kinase inhibition.

Because RAF exhibits significant amino acid homology to other serine/threonine protein kinases, the 5-azaquinoxaline-based compounds of the invention may likely inhibit serine/threonine protein kinases other than RAF. Thus, the methods of the invention also relate to serine/threonine protein kinases other than RAF, including receptor and non-receptor serine/threonine protein kinases.

The methods of the invention also pertain to other compounds that modulate RAF function in cells as the high throughput aspect of the methods allows a wide array of molecules to be tested in a short period of time. Therefore, the methods of the invention can identify existing molecules not disclosed in the present invention that modulate RAF function.

I. Biological Activity of 5-Azaquinoxaline-Based Compounds 5-azaquinoxaline-based compounds of the present invention were tested for their ability to inhibit RAF protein kinase function. The biological assays and results of these inhibition studies are reported herein. The methods used to measure 5-azaquinoxaline-based compound modulation of protein kinase function are similar to those described in PCT WO 98/07695 A1 by Tang et al., and entitled "Indolinone Combinatorial Libraries and Related Products and Methods for the Treatment of Disease," (Lyon & Lyon Docket No. 221/187), filed Aug. 23, 1996, with respect to the high throughput aspect of the method. The PCT WO 98/07695 A1 is incorporated herein by reference in its entirety, including any drawings.

II. Target Diseases to be Treated by 1,4,5-Triazanaphthalene-Based Compounds

The methods, compounds, and pharmaceutical compositions described herein are designed to inhibit cell proliferative disorders by modulating the function of the RAF protein kinase. Proliferative disorders result in unwanted cell proliferation of one or more subsets of cells in a multicellular organism resulting in harm to the organism. The methods, compounds, and pharmaceutical compositions described herein may also be useful for treating and preventing other disorders in organisms, such as disorders related to premature cell death (i.e., neurological diseases) or inflammation. These disorders may be a result of RAF molecules that function inappropriately or a result of RAF-related protein kinase molecules that function inappropriately.

Alterations in the function of the RAF protein kinase or protein kinases related to RAF can lead to enhanced or decreased cell proliferative conditions evident in certain diseases. Aberrant cell proliferative conditions include cancers, fibrotic disorders, mesangial disorders, abnormal angiogenesis and vasculogenesis, wound healing, psoriasis, restenosis, and inflammation.

Fibrotic disorders relate to the abnormal formation of the cellular extracellular matrix. An example of a fibrotic disorder is hepatic cirrhosis. Hepatic cirrhosis is characterized by an increased concentration of extracellular matrix constituents resulting in the formation of a hepatic scar. Hepatic cirrhosis can cause diseases such as cirrhosis of the liver.

Mesangial cell proliferative disorders occur due to the abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies.

Preferred types of cancers that may be treated by the methods and compounds of the invention are lung cancer, ovarian cancer, breast cancer, brain cancer, intra-axial brain cancer, colon cancer, prostate cancer, Kaposi's sarcoma, melanoma, and glioma. Evidence that the compounds and methods of the invention can effectively be utilized to stem and reverse the proliferation of cancer cells is provided herein by reference.

Angiogenic and vasculogenic disorders result from excess proliferation of blood vessels. Blood vessel proliferation is necessary in a variety of normal physiological processes such as embryonic development, corpus luteum formation, wound healing and organ regeneration. However, blood vessel proliferation is also essential in cancer tumor development. Other examples of blood vessel proliferative disorders include arthritis, where new capillary blood vessels invade the joint and destroy cartilage. In addition, blood vessel proliferative diseases include ocular diseases, such as diabetic retinopathy, where new capillaries in the retina invade the vitreous, bleed and cause blindness. Conversely, disorders related to the shrinkage, contraction or closing of blood vessels, such as restenosis, are also implicated in adverse regulation of protein kinases.

Moreover, vasculogenesis and angiogenesis are associated with the growth of malignant solid tumors and metastasis. A vigorously growing cancer tumor requires a nutrient and oxygen rich blood supply to continue growing. As a consequence, an abnormally large number of capillary blood vessels often grow in concert with the tumor and act as supply lines to the tumor. In addition to supplying nutrients to the tumor, the new blood vessels embedded in a tumor provide a gateway for tumor cells to enter the circulation and metastasize to distant sites in the organism. Folkman, 1990, *J. Natl. Cancer Inst.* 82:4–6.

Inappropriate RAF activity can stimulate cell proliferative disorders. Molecules specifically designed to modulate the function of the RAF protein kinase have been shown to inhibit cellular proliferation. Specifically, antisense nucleic acid molecules, which are designed to both bind to message RNA encoding the RAF protein kinase and block translation from that message, effectively reversed transformation of A549 cells in vitro. Monia et al., 1996, *Nature Medicine* 2: 688, incorporated herein by reference in its entirety including all figures and tables. A549 cells are human malignant cells.

These RAF-targeted antisense studies provide evidence that the 5-azaquinoxaline molecules of the invention, which modulate the function of the RAF protein kinase, can stem, and likely reverse, the proliferation of malignant cells in an organism. These 5-azaquinoxaline compounds can be tested in the in vitro methods provided herein by example. Furthermore, the 5-azaquinoxaline compounds may be tested for their effect upon tumor cells in vivo by the xenograft methods also provided herein by example.

There exist at least two ways in which inappropriate RAF activity can stimulate unwanted cell proliferation of a particular type of cells: (1) directly stimulating growth of the particular cell, or (2) increasing vascularization of a particular area, such as tumor tissue, thereby facilitating growth of the tissue.

The use of the present invention is facilitated by first identifying whether the cell proliferation disorder is RAF driven. Once such disorders are identified, patients suffering from such a disorder can be identified by analysis of their symptoms using procedures well known to physicians or veterinarians of ordinary skill in the art. Such patients can then be treated as described herein.

Determining whether the cell proliferation disorder is RAF driven may be accomplished by first determining the level of RAF activity occurring in the cell or in a particular location in a patient's body. For example, in the case of cancer cells the level of one or more RAF activities may be compared for non-RAF driven cancers and RAF driven cancers. If the cancer cells have a higher level of RAF activity than RAF driven cancers, preferably equal to or greater than RAF driven cancers, then they are candidates for treatment using the described RAF-modulating methods and compounds of the invention.

In the case of cell proliferative disorders arising due to unwanted proliferation of non-cancer cells, the level of RAF activity is compared to that level occurring in the general population (e.g., the average level occurring in the general population of people or animals excluding those people or animals suffering from a cell proliferative disorder). If the unwanted cell proliferation disorder is characterized by a higher RAF level than occurring in the general population then the disorder is a candidate for treatment using the described RAF modulating methods and compounds of the invention.

III. Pharmaceutical Compositions and Administration of 5-Azaquinoxaline-Based Compounds Methods of preparing pharmaceutical formulations of the compounds, methods of determining the amounts of compounds to be administered to a patient, and modes of administering compounds to an organism are disclosed in PCT WO98/07695 A1 by Tang et al., and entitled "Indolinone Combinatorial Libraries and Related Products and Methods for the Treatment of Disease," (Lyon & Lyon Docket No. 221/187), filed Aug. 23, 1996, and International patent publication number WO 96/22976, by Buzzetti et al., and entitled "Hydrosoluble 3-Arylidene-2-Oxindole Derivatives as Tyrosine Kinase Inhibitors," published Aug. 1, 1996, both of which are incorporated herein by reference in their entirety, including any drawings. Those skilled in the art will appreciate that such descriptions are applicable to the present invention and can be easily adapted to it.

EXAMPLES

The examples below are non-limiting and are merely representative of various aspects and features of the present invention. The examples describe methods for synthesizing compounds of the invention and methods for measuring an effect of a compound on the function of the RAF protein kinase.

The cells used in the methods are commercially available. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

Example 1

Procedures for Synthesizing 5-Azaquinoxaline-Based Compounds of the Invention

The invention will now be illustrated in the following non-limiting examples in which, unless otherwise stated:

(i) evaporations were carried out by rotary evaporation in vacuo;

(ii) operations were carried out under an atmosphere of an inert gas such as nitrogen;

(iii) high performance liquid chromatography (HPLC) was performed on Merck LiChrosorb RP-18 reversed-phase silica obtained from E. Merck, Darmstadt, Germany;

(iv) yields are given for illustration only and are not necessarily the maximium attainable;

(v) melting points are uncorrected and were determined using a HWS Mainz SG 2000 digital melting point apparatus;

(vi) the structures of all compounds of the formula (I) of this invention were confirmed by proton magnetic resonance spectroscopy on a Bruker AMX500-NMR spectrophotometer, by elemental microanalysis and, in certain cases, by mass spectroscopy;

(vii) the purity of the structures were performed by thin layer chromatography (TLC) using silica gel (Merck Silica Gel 60 F254) or by HPLC; and (viii) intermediates were not generally fully characterised and purity was assessed by thin layer chromatography (TLC) or by HPLC.

Synthetic Procedures

Compound A-2: 6-Benzylamino-3-(4-hydroxyphenyl)-5-azaquinoxaline

4-Hydroxyphenylglyoxal was prepared from 4-hydroxyacetophenone (Lancaster, Acros) according to the published method (J. Amer. Chem. Soc., 71, 1045 (1949)).

2-Amino-6-benzylamino-3-nitropyridine was prepared from 2-amino-6-chloro-3-nitropyridine as follows: 2-Amino-6-chloro-3-nitropyridine (17.35 g, 0.10 mol), benzyl amine (Fluka) (10.72 g, 0.10 mol) and powdered potassium carbonate (10.4 g, 0.035 mol) in n-butanol (100 mL) were heated under reflux for 2 hours. The suspension was filtered and after cooling to room temperature the solid was collected by filtration, washed with butanol, and dried at 50 C. in vacuo to give 2-amino-6-benzylamino-3-nitropyridine (22.2 g, 91%, m.p. 145–146 C.).

6-Benzylamino-3-(4-hydroxyphenyl)-5-azaquinoxaline was prepared from 2-amino-6-benzylamino-3-nitropyridine as follows:

2-Amino-6-benzylamino-3-nitropyridine (25 g, 0.10 mol) was hydrogenated under 5.5 bar of H2 in the presence of 10 g of Raney-Ni in 400 mL of dioxane at 60 C. After 2 hours the reaction mixture was cooled to room temperature, filtrated and 4-hydroxy phenylglyoxal was added and stirred for 2 hours under an argon atmosphere. The suspension was then diluted with water, the solid was collected by filtration, washed with water, recrystallized from 2-propanol, and dried at 50 C. in vacuo to give 6-benzylamino-3-(4-hydroxyphenyl)-5-azaquinoxaline (8 g, 24.4%, m.p. 271–273 C.).

Compound A-1: 6-Phenylamino-3-(4-hydroxyphenyl)-5-azaquinoxaline

By substituting phenylamine in place of benzylamine in the procedure for Compound A-2, the identical process gives 6-phenylamino-3-(4-hydroxyphenyl)-5-azaquinoxaline.

Compound A-3: 6-Methoxy-2-methyl-3-phenyl-5-azaquinoxaline

By substituting 1-phenyl-1,2-propanedione in place of 4-hydroxyphenylglyoxal and methanol in place of benzylamine in the procedure for Compound A-2, the identical process gives 6-methoxy-2-methyl-3-phenyl-5-azaquinoxaline.

Compound A-4: 6-Methoxy-2,3-diphenyl-5-azaquinoxaline

By substituting benzil in place of 4-hydroxyphenylglyoxal and methanol in place of benzylamine in the procedure for Compound A-2 the identical process gives 6-methoxy-2,3-diphenyl-5-azaquinoxaline.

Compound A-5: 6-(4-Fluorobenzylamino)-2-methyl-3-phenyl-5-azaquinoxaline

By substituting 1-phenyl-1,2-propanedione in place of 4-hydroxyphenylglyoxal and 4-fluorobenzylamine in place of benzylamine in the procedure for Compound A-2, the identical process gives 6-(4-fluorobenzylamino)-2-methyl-3-phenyl-5-azaquinoxaline.

Compound A-6: 2,3-Diphenyl-6-(4-fluorobenzylamino)-5-azaquinoxaline

By substituting benzil in place of 4-hydroxyphenylglyoxal and 4-fluorobenzylamine in place of benzylamine in the procedure for Compound A-2 the identical process gives 2,3-diphenyl-6-(4-fluorobenzylamino)-5-azaquinoxaline.

Compound A-7: 3-Phenyl-6-phenylamino-5-azaquinoxaline

By substituting phenylglyoxal in place of 4-hydroxyphenylglyoxal and aniline in place of benzylamine in the procedure for Compound A-2 the identical process gives 3-phenyl-6-phenylamino-5-azaquinoxaline.

Compounds A-8–A-26.

By substituting the appropriate substituted benzylamine in place of benzylamine in the procedure for Compound A-2 the identical process gives the following Compounds:

Compound A-8: 6-(2-Carboxybenzylamino)-3-(4-hydroxyphenyl)-5-azaquinoxaline
Compound A-9: 6-(3-Carboxybenzylamino)-3-(4-hydroxyphenyl)-5-azaquinoxaline
Compound A-10: 6-(4-Carboxybenzylamino)-3-(4-hydroxyphenyl)-5-azaquinoxaline
Compound A-11: 3-(4-Hydroxyphenyl)-6-(2-nitrobenzylamino)-5-azaquinoxaline
Compound A-12: 3-(4-Hydroxyphenyl)-6-(3-nitrobenzylamino)-5-azaquinoxaline
Compound A-13: 3-(4-Hydroxyphenyl)-6-(4-nitrobenzylamino)-5-azaquinoxaline
Compound A-14: 3-(4-Hydroxyphenyl)-6-(2-methylbenzylamino)-5-azaquinoxaline
Compound A-15: 3-(4-Hydroxyphenyl)-6-(3-methylbenzylamino)-5-azaquinoxaline
Compound A-16: 3-(4-Hydroxyphenyl)-6-(4-methylbenzylamino)-5-azaquinoxaline
Compound A-17: 6-(2-Chlorobenzylamino)-3-(4-hydroxyphenyl)-5-azaquinoxaline
Compound A-18: 6-(3-Chlorobenzylamino)-3-(4-hydroxyphenyl)-5-azaquinoxaline
Compound A-19: 6-(4-Chlorobenzylamino)-3-(4-hydroxyphenyl)-5-azaquinoxaline
Compound A-20: 6-(2-Fluorobenzylamino)-3-(4-hydroxyphenyl)-5-azaquinoxaline
Compound A-21: 6-(3-Fluorobenzylamino)-3-(4-hydroxyphenyl)-5-azaquinoxaline
Compound A-22: 6-(4-Fluorobenzylamino)-3-(4-hydroxyphenyl)-5-azaquinoxaline
Compound A-23: 3-(4-Hydroxyphenyl)-6-[2-(trifluoromethyl)benzylamino]-5-azaquinoxaline
Compound A-24: 3-(4-Hydroxyphenyl)-6-[3-(trifluoromethyl)benzylamino]-5-azaquinoxaline
Compound A-25: 3-(4-Hydroxyphenyl)-6-[4-(trifluoromethyl)benzylamino]-5-azaquinoxaline
Compound A-26: 3-(4-Hydroxyphenyl)-6-(phenethyl-1-amino)-5-azaquinoxaline Compounds A-27–A-48.

By substituting the appropriate substituted aniline in place of benzylamine in the procedure for Compound A-2 the identical process gives the following Compounds:

Compound A-27: 6-(2-Carboxyphenylamino)-3-(4-hydroxyphenyl)-5-azaquinoxaline
Compound A-28: 6-(3-Carboxyphenylamino)-3-(4-hydroxyphenyl)-5-azaquinoxaline
Compound A-29: 6-(4-Carboxyphenylamino)-3-(4-hydroxyphenyl)-5-azaquinoxaline
Compound A-30: 3-(4-Hydroxyphenyl)-6-(2-nitrophenylamino)-5-azaquinoxaline
Compound A-31: 3-(4-Hydroxyphenyl)-6-(3-nitrophenylamino)-5-azaquinoxaline
Compound A-32: 3-(4-Hydroxyphenyl)-6-(4-nitrophenylamino)-5-azaquinoxaline
Compound A-33: 3-(4-Hydroxyphenyl)-6-(2-methylphenylamino)-5-azaquinoxaline
Compound A-34: 3-(4-Hydroxyphenyl)-6-(3-methylphenylamino)-5-azaquinoxaline
Compound A-35: 3-(4-Hydroxyphenyl)-6-(4-methylphenylamino)-5-azaquinoxaline Compound A-36: 6-(2-Chlorophenylamino)3-(4-hydroxyphenyl)-5-azaquinoxaline
Compound A-37: 6-(3-Chlorophenylamino)3-(4-hydroxyphenyl)-5-azaquinoxaline
Compound A-38: 6-(4-Chlorophenylamino)3-(4-hydroxyphenyl)-5-azaquinoxaline
Compound A-39: 6-(2-Fluorophenylamino)3-(4-hydroxyphenyl)-5-azaquinoxaline
Compound A-40: 6-(3-Fluorophenylamino)3-(4-hydroxyphenyl)-5-azaquinoxaline
Compound A-41: 6-(4-Fluorophenylamino)3-(4-hydroxyphenyl)-5-azaquinoxaline
Compound A-42: 3-(4-Hydroxyphenyl)-6-[(2-trifluoromethyl)phenylamino]-5-azaquinoxaline
Compound A-43: 3-(4-Hydroxyphenyl)-6-[(3-trifluoromethyl)phenylamino]-5-azaquinoxaline
Compound A-44: 3-(4-Hydroxyphenyl)-6-[(4-trifluoromethyl)phenylamino]-5-azaquinoxaline
Compound A-45: 3-(4-Hydroxyphenyl)-6-(pyrid-2-amino]-5-azaquinoxaline
Compound A-46: 3-(4-Hydroxyphenyl)-6-(pyrid-3-amino]-5-azaquinoxaline
Compound A-47: 3-(4-Hydroxyphenyl)-6-(pyrid-4-amino]-5-azaquinoxaline
Compound A-48: 3-(4-Hydroxyphenyl)-6-(pyrid-2-methylamino]-5-azaquinoxaline Compounds A-49–A-67

By substituting the appropriate substituted benzylamine in place of benzylamine and phenylglyoxal in place of 4-hydroxyphenylglyoxal in the procedure for Compound A-2 the identical process gives the following Compounds:

Compound A-49: 6-(2-Carboxybenzylamino)-3-phenyl-5-azaquinoxaline
Compound A-50: 6-(3-Carboxybenzylamino)-3-phenyl-5-azaquinoxaline
Compound A-51: 6-(4-Carboxybenzylamino)-3-phenyl-5-azaquinoxaline
Compound A-52: 6-(2-Nitrobenzylamino-3-phenyl)-5-azaquinoxaline
Compound A-53: 6-(3-Nitrobenzylamino)-3-phenyl-5-azaquinoxaline
Compound A-54: 6-(4-Nitrobenzylamino)-3-phenyl-5-azaquinoxaline
Compound A-55: 6-(2-Methylbenzylamino)-3-phenyl-5-azaquinoxaline
Compound A-56: 6-(3-Methylbenzylamino)-3-phenyl-5-azaquinoxaline
Compound A-57: 6-(4-Methylbenzylamino)-3-phenyl-5-azaquinoxaline
Compound A-58: 6-(2-Chlorobenzylamino)-3-phenyl-5-azaquinoxaline
Compound A-59: 6-(3-Chlorobenzylamino)-3-phenyl-5-azaquinoxaline
Compound A-60: 6-(4-Chlorobenzylamino)-3-phenyl-5-azaquinoxaline
Compound A-61: 6-(2-Fluorobenzylamino)-3-phenyl-5-azaquinoxaline
Compound A-62: 6-(3-Fluorobenzylamino)-3-phenyl-5-azaquinoxaline
Compound A-63: 6-(4-Fluorobenzylamino)-3-phenyl-5-azaquinoxaline
Compound A-64: 3-Phenyl-6-[2-(trifluoromethyl)benzylamino]-5-azaquinoxaline
Compound A-65: 3-Phenyl-6-[3-(trifluoromethyl)benzylamino]-5-azaquinoxaline
Compound A-66: 3-Phenyl-6-[4-(trifluoromethyl)benzylamino]-5-azaquinoxaline
Compound A-67: 3-Phenyl-6-(phenethyl-1-amino)-5-azaquinoxaline Compounds A-68–A-89

By substituting the appropriate substituted aniline in place of benzylamine and phenylglyoxal in place of 4-hydroxyphenylglyoxal in the procedure for Compound A-2 the identical process gives the following Compounds:

Compound A-68: 6-(2-Carboxyphenylamino)-3-phenyl-5-azaquinoxaline
Compound A-69: 6-(3-Carboxyphenylamino)-3-phenyl-5-azaquinoxaline
Compound A-70: 6-(4-Carboxyphenylamino)-3-phenyl-5-azaquinoxaline
Compound A-71: 6-(2-Nitrophenylamino)-3-phenyl-5-azaquinoxaline
Compound A-72: 6-(3-Nitrophenylamino)-3-phenyl-5-azaquinoxaline
Compound A-73: 6-(4-Nitrophenylamino)-3-phenyl-5-azaquinoxaline
Compound A-74: 6-(2-Methylphenylamino)-3-phenyl-5-azaquinoxaline
Compound A-75: 6-(3-Methylphenylamino)-3-phenyl-5-azaquinoxaline
Compound A-76: 6-(4-Methylphenylamino)-3-phenyl-5-azaquinoxaline
Compound A-77: 6-(2-Chlorophenylamino)-3-phenyl-5-azaquinoxaline
Compound A-78: 6-(3-Chlorophenylamino)3-phenyl-5-azaquinoxaline
Compound A-79: 6-(4-Chlorophenylamino)3-phenyl-5-azaquinoxaline
Compound A-80: 6-(2-Fluorophenylamino)3-phenyl-5-azaquinoxaline
Compound A-81: 6-(3-Fluorophenylamino)3-phenyl-5-azaquinoxaline
Compound A-82: 6-(4-Fluorophenylamino)3-phenyl-5-azaquinoxaline
Compound A-83: 3-Phenyl-6-[(2-trifluoromethyl)phenylamino]-5-azaquinoxaline
Compound A-84: 3-Phenyl-6-[(3-trifluoromethyl)phenylamino]-5-azaquinoxaline
Compound A-85: 3-Phenyl-6-[(4-trifluoromethyl)phenylamino]-5-azaquinoxaline
Compound A-86: 3-Phenyl-6-(pyrid-2-amino]-5-azaquinoxaline
Compound A-87: 3-Phenyl-6-(pyrid-3-amino]-5-azaquinoxaline
Compound A-88: 3-Phenyl-6-(pyrid-4-amino]-5-azaquinoxaline
Compound A-89: 3-Phenyl-6-(pyrid-2-methylamino]-5-azaquinoxaline Compound A-90: 6-Phenylamino-3-(4-methoxyphenyl)-5-azaquinoxaline By substituting 4-methoxyphenyl in place of 4-hydroxyphenyl in the procedure for Compound A-1, the identical process gives 6-phenylamino-3-(4-methoxyphenyl)-5-azaquinoxaline.

Example 2

Assay Measuring Phosphorylating Function of RAF

The following assay reports the amount of RAF-catalyzed phosphorylation of its target protein MEK as well as MEK's target MAPK. The RAF gene sequence is described in Bonner et al., 1985, *Molec. Cell. Biol.* 5: 1400–1407, and is readily accessible in multiple gene sequence data banks. Construction of the nucleic acid vector and cell lines utilized for this portion of the invention are fully described in Morrison et al., 1988, *Proc. Natl. Acad. Sci. USA* 85: 8855–8859.

Materials and Reagents

1. Sf9 (*Spodoptera frugiperda*) cells; GIBCO-BRL, Gaithersburg, Md.
2. RIPA buffer: 20 mM Tris/HCl pH 7.4, 137 mM NaCl, 10% glycerol, 1 mM PMSF, 5 mg/L Aprotenin, 0.5% Triton X-100;
3. Thioredoxin-MEK fusion protein (T-MEK): T-MEK expression and purification by affinity chromatography were performed according to the manufacturer's procedures. Catalog# K 350-01 and R 350-40, Invitrogen Corp., San Diego, Calif.
4. His-MAPK (ERK 2); His-tagged MAPK was expressed in XL1 Blue cells transformed with pUC18 vector encoding His-MAPK. His-MAPK was purified by Ni-affinity chromatography. Cat# 27-4949-01, Pharmacia, Alameda, Calif., as described herein.
5. Sheep anti mouse IgG: Jackson laboratories, West Grove, Pa. Catalog, # 515-006-008, Lot# 28563
6. RAF-1 protein kinase specflc antibody: URP2653 from UBI.
7. Coating buffer: PBS; phosphate buffered saline, GIBCO-BRL, Gaithersburg, Md.
8. Wash buffer: TBST—50 mM Tris/HCL pH 7.2, 150 mM NaCl, 0.1% Triton X-100
9. Block buffer: TBST, 0.1% ethanolamine pH 7.4
10. DMSO, Sigma, St. Louis, Mo.
11. Kinase buffer (KB): 20 mM Hepes/HCl pH 7.2, 150 mM NaCl, 0.1% Triton X-100, 1 mM PMSF, 5 mg/L Aprotenin, 75 M sodium ortho vanadate, 0.5 MM DTT and 10 mM $MgCl_2$.
12. ATP mix: 100 mM $MgCl_2$, 300 M ATP, 10 Ci -$^{33}$P ATP (Dupont-NEN)/mL.
13 Stop solution: 1% phosphoric acid; Fisher, Pittsburgh, Pa.
14. Wallac Cellulose Phosphate Filter mats; Wallac, Turku, Finnland.
15. Filter wash solution: 1% phosphoric acid, Fisher, Pittsburgh, Pa.
16. Tomtec plate harvester, Wallac, Turku, Finnland.
17. Wallac beta plate reader # 1205, Wallac, Turku, Finnland.
18. NUNC 96-well V bottom polypropylene plates for compounds Applied Scientific Catalog # AS-72092.

Procedure

All of the following steps were conducted at room temperature unless specifically indicated.

1. ELISA plate coating: ELISA wells are coated with 100 Lof Sheep anti mouse affinity purified antiserum (1 g/100 L coating buffer) over night at 4 C. ELISA plates can be used for two weeks when stored at 4 C.
2. Invert the plate and remove liquid. Add 100 L of blocking solution and incubate for 30 min.
3. Remove blocking solution and wash four times with wash buffer. Pat the plate on a paper towel to remove excess liquid.
4. Add 1 g of antibody specific for RAF-1 to each well and incubate for 1 hour. Wash as described in step 3.
5. Thaw lysates from RAS/RAF infected Sf9 cells and dilute with TBST to 10 g/100 L. Add 10 g of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10 000×g). Aliquots of lysates are frozen in dry ice/ethanol and stored at −80 C. until use.

6. Remove non-bound material and wash as outlined above (step 3).

7. Add 2 g of T-MEK and 2 g of His-MAEPK per well and adjust the volume to 40 L with kinase buffer. Methods for purifying T-MEK and MAPK from cell extracts are provided herein by example.

8. Predilute compounds (stock solution 10 mg/mL DMSO) or extracts 20 fold in TBST plus 1% DMSO. Add 5 L of the prediluted compounds/extracts to the wells described in step 6. Incubate for 20 min. Controls receive no drug.

9. Start the kinase reaction by addition of 5 L ATP mix; Shake the plates on an ELISA plate shaker during incubation.

10. Stop the kinase reaction after 60 min by addition of 30 L stop solution to each well.

11. Place the phosphocellulose mat and the ELISA plate in the Tomtec plate harvester. Harvest and wash the filter with the filter wash solution according to the manufacturers recommendation. Dry the filter mats. Seal the filter mats and place them in the holder. Insert the holder into radioactive detection apparatus and quantify the radioactive phosphorous on the filter mats.

Alternatively, 40 L aliquots from individual wells of the assay plate can be transferred to the corresponding Positions on the phosphocellulose filter mat. After air-drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantify the radioactive phosphorous on the filter mats.

$IC_{50}$ values were measured according to the protocol for the following 5-azaquinoxaline-based compounds in the RAF-1 ELISA assay:

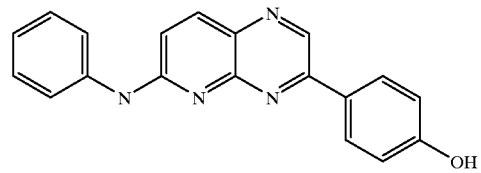

(A-1)

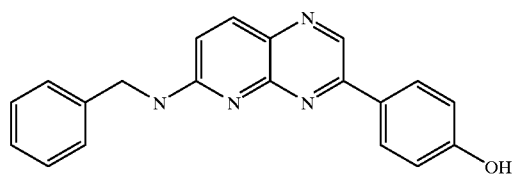

(A-2)

-continued

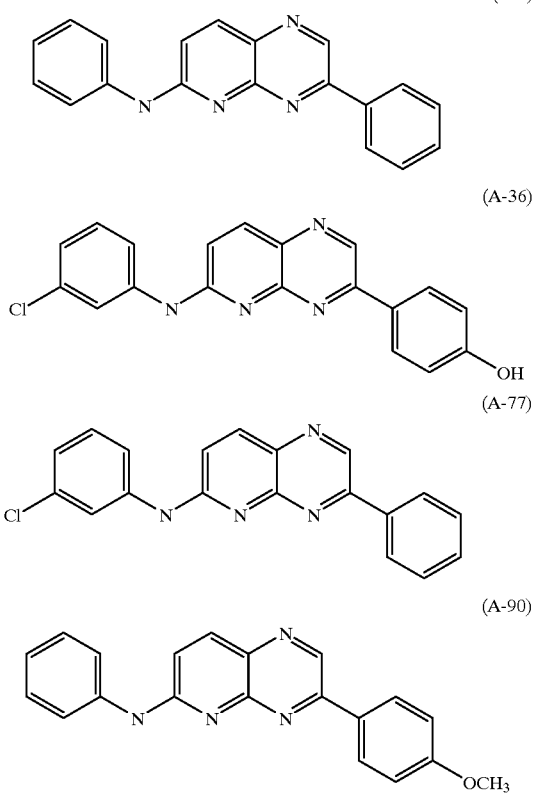

An IC$_{50}$ value is the concentration of the 5-azaquinoxaline-based inhibitor required to decrease the maximum amount of phosphorylated target protein or cell growth by 50%. The IC$_{50}$ values measured in the RAF-1 phosphorylation assay are depicted in Table 1:

TABLE 1

| Compound | IC$_{50}$ ( M) |
|---|---|
| A-1 | 11.5 |
| A-2 | 7.8 |
| A-7 | 33 |
| A-36 | 45.6 |
| A-77 | 20.3 |
| A-90 | 98.0 |

Example 3

Purification of MAPK and MEK

The MAPK and MEK proteins are readily expressed in cells by sublconing a gene encoding these proteins into a commercially available vector that expresses the proteins with a poly-Histidine tag. Genes encoding these proteins are readily available from laboratories that normally work with these proteins or by cloning these genes from cells containing cDNA libraries. The libraries are readily commercially available and a person skilled in the art can readily design nucleic acid probes homologous to cDNA molecules encoding MEK or MAPK from the nucleic acid sequences of MEK and MAPK, available in multiple gene data bases such as Genbank. The cloning of a gene can be accomplished in a short time period using techniques currently available to persons skilled in the art.

Purification of the MEK and MAPK proteins from cell extracts can be accomplished using the following protocol, which is adapted from Robbins et al., 1993, J. Biol. Chem. 268: 5097–5106:

1. Lyse cells by sonication, osmotic stress, or French Press techniques readily available to persons skilled in the art. An appropriate sonication buffer is provided below.

2. Equilibrate a solid support which is conjugated with nickel or cobalt with the equilibration buffer disclosed below. The poly-histidine tag specifically binds to the nickel and cobalt atoms on the solid support. Equilibration can be achieved by washing the resin three times with a volume of the equilibration buffer equal to ten times the volume of the solid support. The solid support is readily available to persons of ordinary skill in the art.

3. Add the cell lysate to the solid support and equilibrate in a vessel for a period of time. Alternatively, the solid support can be packed within a protein chromatography column and the lysate may be flowed through the solid support.

4. Wash the solid support with the wash buffer disclosed below.

5. Elute the MEK or MAPK protein from the solid support with an amount of elution buffer (provided below) that removes a significant portion of the protein from the solid support.

Sonication Buffer
50 mM sodium phosphate pH 8.0
0.3 M sodium chloride
10 mM-mercaptoethanol
1% NP40
10 mM NaF
0.5 mM Pefablock Equilibration Buffer
50 mM sodium phosphate pH 8.0
0.3 M sodium chloride
10 mM-mercaptoethanol
1% NP40
10mM NaF
1 mM Imidazol Wash Buffer
50 mM sodium phosphate pH 8.0
0.3 M sodium chloride
10 mM-mercaptoethanol
1% NP40
10 mM NaF
10 mM Imidazol Elution Buffer
50 mM sodium phosphate pH 8.0
0.3 M sodium chloride
10 mM-mercaptoethanol
1% NP40
10mM NaF
10–500 mM Imidazol Example 4

Assay Measuring Phosphorlating Function of EGF Receptor

EGF Receptor kinase activity (EGFR-NIH3T3 assay) in whole cells was measured as described in detail in PCT Publication WO9640116, filed Jun. 5, 1996, by Tang et al., and entitled "Indolinone Compounds for the Treatment of Disease," incorporated herein by reference in its entirety, including any drawings.

The IC$_{50}$ values measured in the EGF receptor phosphorylation assay are depicted in Table 2:

TABLE 2

| Compound | IC$_{50}$ ($\mu$M) |
|---|---|
| A-2 | >50 |
| A-3 | >100 |
| A-4 | >100 |
| A-5 | >100 |
| A-6 | >100 |
| A-7 | >50 |

Example 5

Assay Measuring the Effect of 5-Azaquinoxaline-Based Compounds on the Growth of Cells Expressing RAS The following assay measures growth rates for NIH-3T3 cells expressing RAS. The purpose of the assay is to determine the effects of compounds on the growth of NIH 3T3 cells over expressing H-Ras.

Materials
96-well flat bottom sterile plates
96-well round bottom sterile plates
sterile 25 mL or 100 mL reservoir
pipets, multi-channel pipetman
sterile pipet tips
sterile 15 mL and 50 mL tubes Reagents
0.4% SRB in 1% acetic acid
10 mM Tris base
10% TCA
1% acetic acid
sterile DMSO (Sigma)
compound in DMSO (100 mM or less stock solution)
Trypsin-EDTA (GIBCO BRL)

Cell Line
3T3/H-Ras (NIH 3T3 clone 7 cells expressing genomic fragment of oncogenic H-Ras).

The cells can be constructed using the following protocol:
1. Subclone a gene fragment encoding Ras into a commercially available vector that will stably transfect NIH-3T3 cells. The fragment is from the genomic transforming allele of cHa-ras.
2. Transfect NIH-3T3 cells with the subcloned vector by a calcium phosphate method. Select cells expressing the Ras construct in 2% serum in DMEM. Visible foci are observed after 2 weeks. Pool the transformed cells to generate a stably transformed cell line.

Growth Medium
2% calf serum/DMEM+2 mM glutamine, Pen/Strep

Protocol

Day 0: Cell Plating:
This part of assay is carried out in a laminar flow hood.
1. Trypsinize cells. Transfer 200 $\mu$L of cell suspension to 10 mL of isotone. Count cells with a Coulter Counter.
2. Dilute cells in growth medium to 60,000 cell/mL. Transfer 100 $\mu$L of cells to each well in a 96-well flat bottom plate to give 6000 cells/well.
3. Use half of plate (4 rows) for each comound and quadruplicate wells for each comound concentration, and a set of 4 wells for medium control.
4. Gently shake plates to allow for uniform attachment of the cells.
5. Incubate the plates at 37 C. in a 10% CO$_2$ incubator.

Day 1: Addition of Compound:
This part of assay is carried out in a laminar flow hood.

1. In a 96-well round bottom plate, add 120 $\mu$L of growth medium containing 2× final % DMSO found in highest screening concentration of compound to columns 1 to 11. For example, if the highest concentration is 100 $\mu$L, and this is made from a 100 mM stock, 1× DMSO is 0.1%, so 2× DMSO is 0.2%. This plate is used to titrate out the compound, 4 rows per compound.

2. In a sterile 15 mL tube, make a 2× solution of the highest screening concentration of compound in growth medium plus 2× DMSO. 1 mL per cell line is needed. The starting concentration of the compound is usually 100 $\mu$M but this concentration may vary depending upon the solubility of the compound.

3. Transfer 240 $\mu$L of the 2× starting compound solution to qudruplicate wells in column 12 of the 96-well round bottom plate. Do 1:2 serial dilutions across the plate from right to left by transferring 12 $\mu$L from column 12 to column 11, column 11 to 10 and so on through column 2. Transfer 100 $\mu$L of compound dilutions, and 100 $\mu$L of medium in column 1, onto 100 $\mu$L medium on cells in corresponding wells of 96-well flat bottom plate. Total volume per well should be 200 $\mu$L.

4. Return the plate to the incubattor and incubate for 3 days.

Day 4: Development of Assay
This party of assay is carried out on the bench.
1. Aspirate or pour off medium. Add 200 $\mu$L cold 10% TCA to each well to fix cells. Incubate plate for at least 60 min. at 4 C.
2. Discard TCA and rinse wells 5 times with tap water. Dry plates upside down on paper towels.
3. Stain cells with 100 $\mu$L/well 0.4% SRB for 10 min.
4. Pour of SRB and rinse wells 5 times with 1% acetic acid. Dry plates completely upside down on paper towels.
5. Solubilize dye with 100 $\mu$L/well 10 mM Tris base for 5–10 min. on shaker.
6. Read plates on Dynatech ELISA Plate REader at 570 nm with reference at 630 nm.

Select compounds inhibited the growth rate of cells over-expressing RAS as illustrated in Table 3.

TABLE 3

| Compound | IC$_{50}$ ($\mu$M) RAS/NIH3T3 |
|---|---|
| A-1 | 1.04 |
| A-2 | 7.6 |
| A-6 | 13.5 |
| A-36 | 0.18 |
| A-77 | 0.7 |

Example 6

Assay Measuring Effect of 5-Azaquinoxaline-Based Compounds on Growth of A549 Cells The following assay measures growth rates for A549 cells. The purpose of the assay is to determine the effects of compounds on the growth of A549 human lung carcinoma cells. A549 cells are readily accessible from commercial sources, such as ATCC (CCL185).

Materials
96-well flat bottom sterile plates
96-well round bottom sterile plates
sterile 25 mL or 100 mL reservoir
pipets, multi-channel pipetman
sterile pipet tips sterile 15 mL and 50 mL tubes
Reagents
0.4% SRB in 1% acetic acid
10 mM Tris base
10% TCA
1% acetic acid
sterile DMSO (Sigma)
compound in DMSO (100 mM or less stock solution)
Trypsin-EDTA (GIBCO BRL)
Cell Line and Growth Medium
A549 human lung carcinoma cells (ATCC CCL185)
10% fetal calf serum in Ham's F12-K
Protocol
Day 0: Cell Plating:
This part of assay is carried out in a laminar flow hood.
1. Trypsinize cells. Transfer 200 L of cell suspension to 10 mL of isotone. Count cells with a Coulter Counter.
2. Dilute cells in growth medium to 20,000 cell/mL. Transfer 100 L of cells to each well in a 96-well flat bottom plate to give 2000 cells/well.
3. Use half of plate (4 rows) for each compound and quadruplicate wells for each compound concentration, and a set of 4 wells for medium control.
4. Gently shake plates to allow for uniform attachment of the cells.
5. Incubate the plates at 37 C. in a 10% CO2 incubator.
Day 1: Addition of Compound:
This part of assay is carried out in a laminar flow hood.
1. In a 96 well-round bottom plate, add 120 L of growth medium containing 2× final % DMSO found in highest screening concentration of compound to columns 1 to 11. For example, if the highest screening concentration is 100 M, and this is made from a 100 mM stock, 1× DMSO is 0.1%, so 2× DMSO is 0.2%. This plate is used to titrate out the compound, 4 rows per compound.
2. In a sterile 15 mL tube, make a 2× solution of the highest screening concentration of compound in growth medium plus 2× DMSO. 1 mL per cell line is needed. The starting concentration of the compound is usually 100 M but this concentration may vary depending upon the solubility of the compound.
3. Transfer 240 L of the 2× starting compound solution to quadruplicate wells in column 12 of the 96-well round bottom plate. Do 1:2 serial dilutions across the plate from right to left by transferring 120 L from column 12 to column 11, column 11 to 10 and so on through column 2. Transfer 100 L of compound dilutions, and 100 L of medium in column 1, onto 100 L medium on cells in corresponding wells of 96-well flat bottom plate. Total volume per well should be 200 L.
4. Return the plate to the incubator and incubate for 3 days.
Day 5: Development of Assay
This part of assay is carried out on the bench.
1. Aspirate or pour off medium. Add 200 L cold 10% TCA to each well to fix cells. Incubate plate for at least 60 min. at 4 C.
2. Discard TCA and rinse wells 5 times with tap water. Dry plates upside down on paper towels.
3. Stain cells with 100 L/well 0.4% SRB for 10 min.
4. Pour off SRB and rinse wells 5 times with 1% acetic acid. Dry plates completely upside down on paper towels.
5. Solubilize dye with 100 L/well 10 mM Tris base for 5–10 min. on shaker.
6. Read plates on Dynatech ELISA Plate Reader at 570 nm with reference at 630 nm.
Select compounds inhibited the growth rates of A549 cells, as illstrated in Table 4.

TABLE 4

| Compound | $IC_{50}$ ( M) A549 |
|---|---|
| A-2 | 25.1 |
|  | >10 (2% FBS) |
| A-6 | 23.8 |
|  | >10 (2% FBS) |

Example 7

Method for Determining the Biological Activity of RAF Modulators in Vivo

Xenograft studies can be utilized to monitor the effect of compounds of the invention upon the inhibition of ovarian, melanoma, prostate, lung and mammary tumor cells. The protocol for the assay is described in detail in PCT Publication WO9640116, filed Jun. 5, 1996, by Tang et al., and entitled "Indolinone Compounds for the Treatment of Disease," incorporated herein by reference in its entirety, including any drawings.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Those references not previously incorporated herein by reference, including both patent and non-patent references, are expressly incorporated herein by reference for all purposes. Other embodiments are within the following claims.

What is claimed is:

1. A method of preventing or treating an abnormal condtion in a mammal, wherein said abnormal condition is associated with an aberration in a signal transduction pathway characterized by an interaction between the serine/threonine protein kinase RAF and a natural binding partner, said method comprising the step of administering a 5-azaquinoxaline-based compound of formula I to said organism

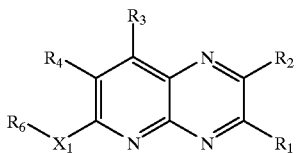

(I)

wherein $R_3$ and $R_4$ are hydrogen, $R_1$ and $R_2$ are independently selected from the group consisting of hydrogen, methyl, phenyl and 4-hydroxyphenyl, and $R_6$ and $X_1$ substituents together form a moiety selected from the group consisting of methoxy, benzylamino, 4-fluorobenzylamino, 2-carboxybenzylamino, 3-carboxybenzylamino, 4-carboxybenzylamino, 2-nitrobenzylamino, 3-nitrobenzylamino, 4-nitrobenzylamino, 2-methylbenzylamino, 3-methylbenzylamino, 4-methylbenzylamino, 2-chlorobenzylamino, 3-chlorobenzylamino, 4-chlorobenzylamino, 2-fluorobenzylamino, 3-fluorobenzylamino, 4-fluorobenzylamino, 2-(trifluoromethyl)benzylamino, 3-(trifluoromethyl)benzylamino, 4-(trifluoromethyl)benzylamino, phenethyl-1-amino, phenylamino, 2-carboxyphenylamino, 3-carboxyphenylamino, 4-carboxyphenylamino, 2-nitrophenylamino, 3-nitrophenylamino, 4-nitrophenylamino, 2-methylphenylamino, 3-methylphenylamino, 4-methylphenylamino, 2-chlorophenylamino, 3-chlorophenylamino, 4-chlorophenylamino, 2-fluorophenylamino, 3-fluorophenylamino, 4-fluorophenylamino, 2-(trifluoromethyl)phenylamino, 3-(trifluoromethyl)phenylamino, 4-(trifluoromethyl)phenylamino, pyrid-2-amino, pyrid-3-amino, pyrid-4-amino, and pyrid-2-methylamino.

2. The method of claim 1, wherein said abnormal condition is cancer or a fibrotic disorder.

3. The method of claim 2, wherein said abnormal condition is a cancer selected from the group consisting of lung cancer, ovarian cancer, breast cancer, brain cancer, intraaxial brain cancer colon cancer, prostate cancer, sarcoma, Kaposi's sarcoma melanoma, and glioma.

4. A 5-azaquinoxaline-based compound having a structure set forth in formula I:

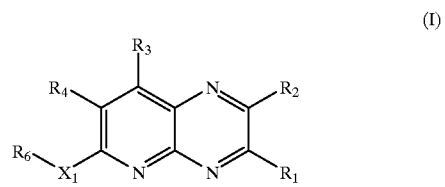

(I)

wherein $R_3$ and $R_4$ are hydrogen, $R_1$ and $R_2$ are independently selected from the group consisting of hydrogen, methyl, phenyl and 4-hydroxyphenyl, and $R_6$ and $X_1$ substituents together form a moiety selected from the group consisting of methoxy, benzylamino, 4-fluorobenzylamino, 2-carboxybenzylamino, 3-carboxybenzylamino, 4carboxybenzylamino, 2-nitrobenzylamino, 3-nitrobenzylamino, 4-nitrobenzylamino, 2-methylbenzylamino, 3-methylbenzylamino, 4-methylbenzylamino, 2-chlorobenzylamino, 3-chlorobenzylamino, 4-chlorobenzylamino, 2-fluorobenzylamino, 3-fluorobenzylamino, 4-fluorobenzylamino, 2-(trifluoromethyl)benzylamino, 3-(trifluoromethyl)benzylamino, 4-(trifluoromethyl)benzylamino, phenethyl-1-amino, phenylamino, 2-carboxyphenylamino, 3-carboxyphenylamino, 4-carboxyphenylamino, 2-nitrophenylamino, 3-nitrophenylamino, 4-nitrophenylamino, 2-methylphenylamino, 3-methylphenylamino, 4-methylphenylamino, 2-chlorophenylamino, 3-chlorophenylamino, 4-chlorophenylamino, 2-fluorophenylamino, 3-fluorophenylamino, 4-fluorophenylamino, 2-(trifluoromethyl)phenylamino, 3-(trifluoromethyl)phenylamino, 4-(trifluoromethyl)phenylamino, pyrid-2-amino, pyrid-3-amino, pyrid-4-amino, and pyrid-2-methylamino.

5. A pharmaceutical composition comprising a 5-azaquinoxaline compound of claim 4 or salt thereof, and a physiologically acceptable carrier or diluent.

* * * * *